(12) United States Patent
Tom

(10) Patent No.: US 6,759,534 B2
(45) Date of Patent: Jul. 6, 2004

(54) PROCESS AND INTERMEDIATES FOR PYRIDAZINONE ANTIDIABETIC AGENTS

(75) Inventor: Norma J. Tom, Waterford, CT (US)

(73) Assignee: Pfizer Inc., New York, NY (US)

( * ) Notice: Subject to any disclaimer, the term of this patent is extended or adjusted under 35 U.S.C. 154(b) by 9 days.

(21) Appl. No.: 10/337,635

(22) Filed: Jan. 7, 2003

(65) Prior Publication Data

US 2003/0162969 A1 Aug. 28, 2003

Related U.S. Application Data

(60) Provisional application No. 60/347,679, filed on Jan. 9, 2002.

(51) Int. Cl.⁷ ............................................. C07D 405/12
(52) U.S. Cl. ..................................................... 544/238
(58) Field of Search ......................................... 544/238

(56) References Cited

FOREIGN PATENT DOCUMENTS

| EP | 135076 A2 * | 7/1984 | |
| WO | WO 02079198 | 10/2002 | ......... C07D/405/12 |

* cited by examiner

*Primary Examiner*—Mukund J. Shah
*Assistant Examiner*—Thomas McKenzie
(74) *Attorney, Agent, or Firm*—Peter C. Richardson; Gregg C. Benson; Carl J. Goddard

(57) ABSTRACT

The present invention relates to a process for preparing pyridazinone aldose reductase inhibitors which are useful in the prevention and/or treatment of diabetic complications such as diabetic neuropathy, diabetic retinopathy, diabetic nephropathy, diabetic cardiomyopathy, diabetic microangiopathy and diabetic macroangiopathy in mammals. The invention also relates to novel intermediates useful in preparing those aldose reductase inihibitors.

14 Claims, No Drawings

PROCESS AND INTERMEDIATES FOR PYRIDAZINONE ANTIDIABETIC AGENTS

This application is filed claiming priority from U.S. Application No. 60/347,679 filed Jan. 9, 2002.

FIELD OF THE INVENTION

The present invention relates to a process for preparing sulfonyl pyridazinone aldose reductase inhibitors. The present invention also relates to novel intermediates used in the process to prepare those aldose reductase inhibitors. Accordingly, the compounds prepared by the process of this invention lower sorbitol levels and, thus, lower fructose levels and have utility in the treatment and/or prevention of diabetic complications such as diabetic neuropathy, diabetic retinopathy, diabetic nephropathy, diabetic cardiomyopathy, diabetic microangiopathy and diabetic macroangiopathy in mammals.

BACKGROUND OF THE INVENTION

The enzyme aldose reductase is involved in regulating the reduction of aldoses, such as glucose and galactose, to their corresponding polyols, such as sorbitol and galactitol. Sulfonyl pyridazinone compounds of Formula I of this invention, prodrugs of such compounds and pharmaceutically acceptable salts of such compounds and prodrugs, are useful as aldose reductase inhibitors in the treatment and prevention of diabetic complications of humans and other mammals associated with increased polyol levels in certain tissues (e.g., nerve, kidney, lens and retina tissue) of affected humans and other mammals.

Commonly assigned U.S. Provisional Patent Application No. 60/280,051, which is incorporated herein by reference, discloses compounds of the formula

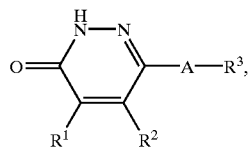

wherein A, $R^1$, $R^2$ and $R^3$ are defined as set forth therein.

SUMMARY OF THE INVENTION

This invention is directed to a process for preparing a compound of the formula

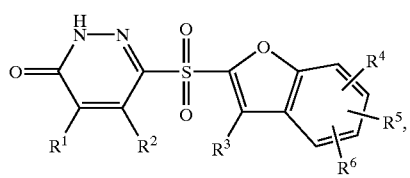

I wherein $R^1$ and $R^2$ are each independently hydrogen or methyl; and $R^3$, $R^4$, $R^5$ and $R^6$ are each independently H, halo, formyl, $(C_1-C_6)$alkyl optionally substituted with up to three fluoro, $(C_1-C_6)$alkoxy optionally substituted with up to three fluoro, $(C_1-C_6)$alkoxycarbonyl, $(C_1-C_6)$alkylenyloxycarbonyl, $(C_1-C_4)$alkoxy-$(C_1-C_4)$alkyl, $(C_1-C_4)$alkylcarbonylamido, $(C_3-C_7)$cycloalkylcarbonylamido, phenylcarbonylamido, benzyl, phenyl or naphthyl, wherein said benzyl, phenyl and naphthyl are optionally independently with up to two substituents independently selected from halo, $(C_1-C_6)$alkyl optionally substituted with up to three fluoro, $(C_1-C_6)$alkoxy optionally substituted with up to three fluoro and $(C_1-C_4)$alkoxy-$(C_1-C_4)$alkyl;

comprising the consecutive steps of:

(a) reacting a compound of the formula

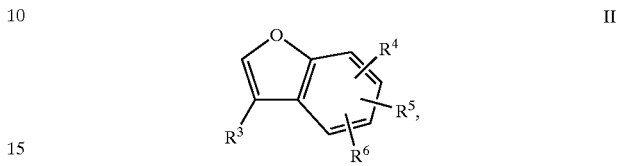

II wherein $R^3$, $R^4$, $R^5$ and $R^6$ are each independently defined as set forth above, with an organolithium compound in the presence of a sulfur source in a first reaction inert solvent to form the reactive intermediate

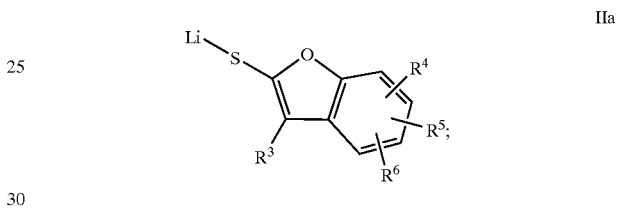

IIa (b) reacting said reactive intermediate IIa with a compound of the formula

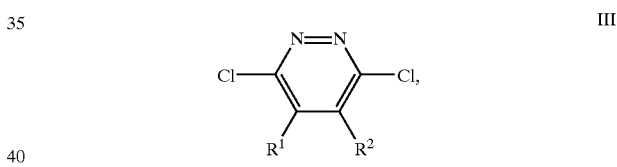

III to form a compound of the formula

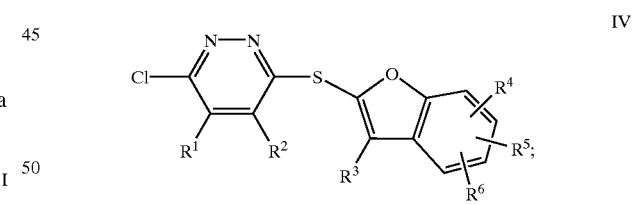

IV (c) reacting said compound of the formula IV with an alkaline $(C_1-C_2)$alkoxide in a $(C_1-C_2)$alkanol to form an ether compound of the formula

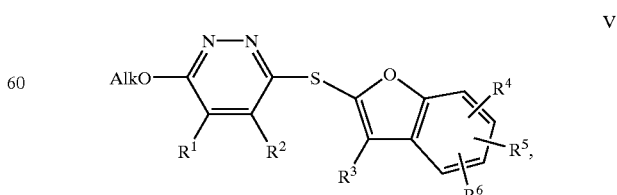

V wherein Alk is $(C_1-C_2)$alkyl;

(d) reacting said compound of the formula V with a mineral acid to form a compound of the formula

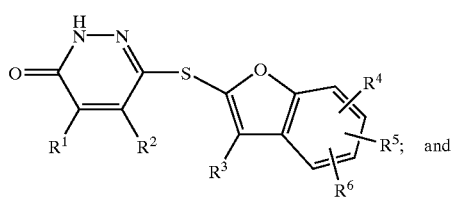

(e) oxidizing said compound of the formula VI in a second reaction inert solvent to form a compound of the formula I.

In a preferred process of this invention, step (c) and step (d) are performed together in situ. In a further preferred process of this invention, in step (a) said organolithium compound is n-butyllithium, said first reaction inert solvent is tetrahydrofuran and said sulfur source is $S_8$; in step (c) said alkaline $(C_1-C_2)$alkoxide is sodium methoxide and said $(C_1-C_2)$alkanol is methanol; and in step (d) said compound of formula VI is oxidized with urea-hydrogen peroxide in the presence of trifluoroacetic anhydride and said second reaction inert solvent is tetrahydrofuran.

In a still further preferred process of this invention, $R^3$, $R^4$, $R^5$ and $R^6$ are each independently hydrogen, methyl, methoxy, chloro, fluoro, ethyl, 4-fluorophenyl, trifluoromethyl, isopropyl or phenyl. In a still further preferred process of this invention, $R^1$, $R^2$, $R^4$ and $R^5$ are each hydrogen; $R^3$ is 3-methyl and $R^6$ is 5-chloro.

This invention is also directed to compounds of the formula

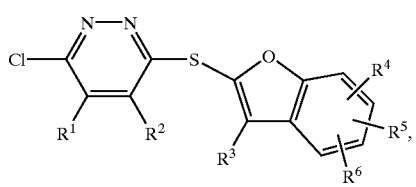

and pharmaceutically acceptable salts thereof, wherein $R^1$ and $R^2$ are each independently hydrogen or methyl; and $R^3$, $R^4$, $R^5$ and $R^6$ are each independently H, halo, formyl, $(C_1-C_6)$alkyl optionally substituted with up to three fluoro, $(C_1-C_6)$alkoxy optionally substituted with up to three fluoro, $(C_1-C_6)$alkoxycarbonyl, $(C_1-C_6)$alkylenyloxycarbonyl, $(C_1-C_4)$alkoxy-$(C_1-C_4)$alkyl, $(C_1-C_4)$alkylcarbonylamido, $(C_3-C_7)$cycloalkylcarbonylamido, phenylcarbonylamido, benzyl, phenyl or naphthyl, wherein said benzyl, phenyl and naphthyl are optionally independently with up to two substituents independently selected from halo, $(C_1-C_6)$alkyl optionally substituted with up to three fluoro, $(C_1-C_6)$alkoxy optionally substituted with up to three fluoro and $(C_1-C_4)$alkoxy-$(C_1-C_4)$alkyl.

A preferred group of compounds of formula IV of this invention are those compounds, designated as Group A, and pharmaceutically acceptable salts thereof, wherein $R^3$, $R^4$, $R^5$ and $R^6$ are each independently hydrogen, methyl, methoxy, chloro, fluoro, ethyl, 4-fluorophenyl, trifluoromethyl, isopropyl or phenyl.

A preferred compound of this invention is the compound wherein $R^1$, $R^2$, $R^4$ and $R^5$ are each hydrogen; $R^3$ is 3-methyl and $R^6$ is 5-chloro, having the structure

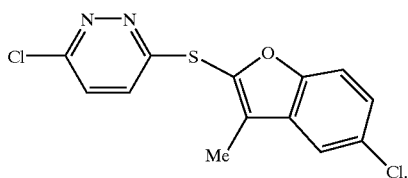

This invention is also directed to a process for preparing a compound of the formula IV above wherein $R^1$ and $R^2$ are each independently hydrogen or methyl; $R^3$, $R^4$, $R^5$ and $R^6$ are each independently H, halo, formyl, $(C_1-C_6)$alkyl optionally substituted with up to three fluoro, $(C_1-C_6)$alkoxy optionally substituted with up to three fluoro, $(C_1-C_6)$alkoxycarbonyl, $(C_1-C_6)$alkylenyloxycarbonyl, $(C_1-C_4)$alkoxy-$(C_1-C_4)$alkyl, $(C_1-C_4)$alkylcarbonylamido, $(C_3-C_7)$cycloalkylcarbonylamido, phenylcarbonylamido, benzyl, phenyl or naphthyl, wherein said benzyl, phenyl and naphthyl are optionally independently with up to two substituents independently selected from halo, $(C_1-C_6)$alkyl optionally substituted with up to three fluoro, $(C_1-C_6)$alkoxy optionally substituted with up to three fluoro and $(C_1-C_4)$alkoxy-$(C_1-C_4)$alkyl;

comprising the consecutive steps of:

(a) reacting a compound of the formula II wherein $R^3$, $R^4$, $R^5$ and $R^6$ are each independently defined as set forth above with an organolithium compound in the presence of a sulfur source in a reaction inert solvent to form a reactive intermediate of the formula IIa; and (b) reacting said reactive intermediate IIa with a compound of the formula III to form a compound of the formula IV.

In that process, it is preferred that said organolithium compound is n-butyllithium, said reaction inert solvent is tetrahydrofuran and said sulfur source is $S_8$. It is particularly preferred that $R^3$, $R^4$, $R^5$ and $R^6$ are each independently hydrogen, methyl, methoxy, chloro, fluoro, ethyl, 4-fluorophenyl, trifluoromethyl, isopropyl or phenyl. It is still further preferred that $R^1$, $R^2$, $R^4$ and $R^4$ are each hydrogen; $R^3$ is 3-methyl and $R^6$ is 5-chloro.

This invention is also directed to a process for preparing the compound of the formula

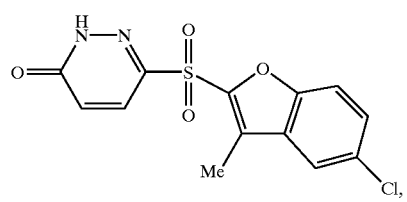

comprising the consecutive steps of:

(a) reacting the compound of the formula

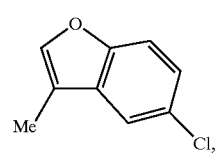

with n-butyllithium in the presence of $S_8$ in tetrahydrofuran to form the reactive intermediate XIIa

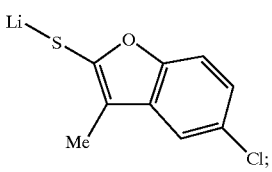

(b) reacting said reactive intermediate XIIa with the compound of the formula

XIII

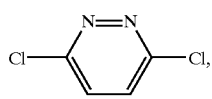

to form the compound of the formula

XIV

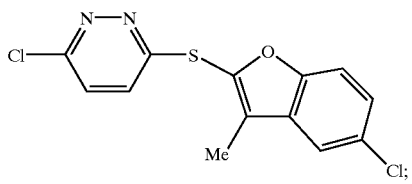

(c) reacting said compound of the formula XIV with sodium methoxide in methanol to form the compound of the formula

XV

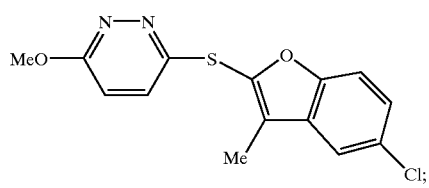

(d) reacting said compound of the formula XV with concentrated hydrochloric acid to form the compound of the formula

XVI

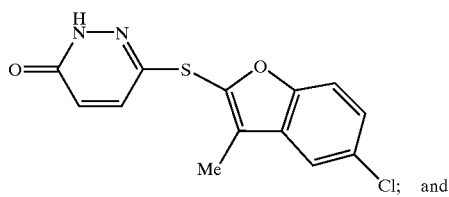

(e) oxidizing said compound of the formula XVI with hydrogen peroxide-urea complex in the presence of trifluoroacetic anhydride in tetrahydrofuran to form the compound of the formula XI. It is particularly preferred that step (c) and step (d) are performed in situ.

The subject invention also includes isotopically-labeled compounds, which are identical to those recited in Formula IV, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of Formula IV of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ or $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of Formula IV of this invention and prodrugs thereof can generally be prepared by carrying out the procedures disclosed in the Schemes and/or in the Examples below, by substituting a readily available isotopically labeled reagent for a non-isotopically labeled reagent. The invention also includes processes of this invention whereby isotopically labeled compounds are used therein.

By "halo" is meant chloro, bromo, iodo, or fluoro.

By "alkyl" is meant straight or branched chain saturated hydrocarbon or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By "alkoxy" is meant straight chain saturated alkyl or branched saturated alkyl bonded through an oxygen. Exemplary of such alkoxy groups (assuming the designated length encompasses the particular example) are methoxy, ethoxy, propoxy, isopropoxy, butoxy, isobutoxy and tertiary butoxy. By "alkoxide" is meant straight chain saturated alkyl or branched saturated alkyl having a negative charge on the oxygen. Exemplary of such alkoxide groups (assuming the designated length encompasses the particular example) are methoxide, ethoxide, propoxide, isopropoxide, butoxide, isobutoxide and tertiary butoxide.

The expression "pharmaceutically acceptable salts" refers to pharmaceutically acceptable acid addition. The expression "pharmaceutically-acceptable acid addition salts" is intended to include, but is not limited to, such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts. A particularly preferred salt is the sodium salt.

The pharmaceutically acceptable acid addition salts of the compounds of this invention may be readily prepared by reacting the free base form of said compounds with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent. They can be further purified by crystallization from ($C_1$–$C_6$)alcoholic solvents such as methanol, ethanol or isopropanol or from ketonic solvents such as acetone, methyl ethyl ketone or methyl isobutyl ketone.

As used herein, the expressions "reaction inert solvent" and "inert solvent" refer to a solvent or mixture of solvents which does not interact with starting materials, reagents, intermediates or products in a manner which adversely affects the yield of the desired product.

As used herein, the term "reactive intermediate" refers to a compound which is formed during the course of a reaction which is not isolated. A reactive intermediate is generally a compound which is not isolatable under ordinary conditions and which is "quenched" by the addition of another reagent which reacts with the reactive portion of the reactive intermediate.

The term "in situ," where used herein, indicates that two steps are carried out in one reaction vessel without isolation of an intermediate compound which could have been isolated if so desired.

Hydrates and solvates of the compounds of this invention are also included.

The chemist of ordinary skill in the art will also recognize that certain compounds of Formula I of this invention can exist in tautomeric form, i.e., that an equilibrium exists between two isomers which are in rapid equilibrium with each other. A common example of tautomerism is keto-enol tautomerism, i.e.,

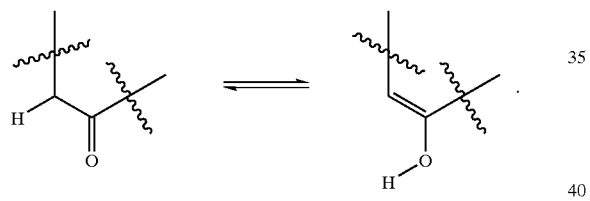

Examples of compounds which can exist as tautomers include hydroxypyridines, hydroxypyrmidines and hydroxyquinolines. In particular, a person skilled in the art will recognize that the pyridazinones of the instant invention can exist as two separate tautomers, e.g.,

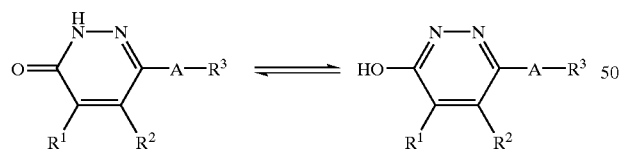

Generally, in this application, the tautomeric forms of such compounds are depicted and named as a pyridazinone. However, the skilled person will recognize that such compounds may also be depicted and/or named as a hydroxypyridazine. Other examples will be recognized by those skilled in the art. All such tautomers and mixtures thereof are included in the compounds that are prepared by the processes of this invention.

Whenever the structure of a cyclic radical is shown with a bond drawn from outside the ring to inside the ring, it will be understood by those of ordinary skill in the art to mean that the bond may be attached to any atom on the ring with an available site for bonding. If the cyclic radical is a bicyclic or tricyclic radical, then the bond may be attached to any atom on any of the rings with an available site for bonding. For example,

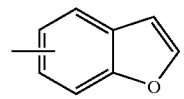

represents any or all of the following radicals:

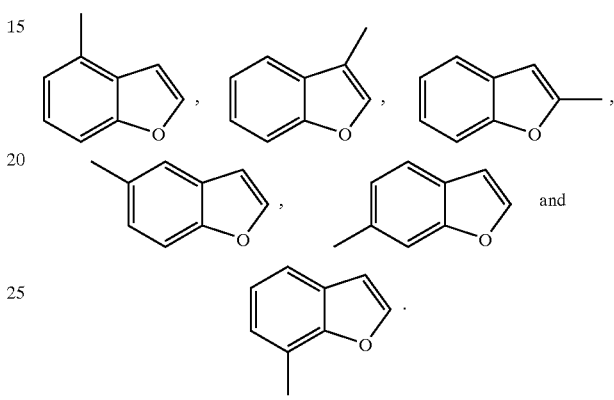

Other features and advantages will be apparent from the specification and claims which describe the invention.

DETAILED DESCRIPTION OF THE INVENTION

The compounds of formula IV (1-4 in Scheme I) of this invention are intermediates in the synthesis of the potent aldose reductase compounds of Formula I. The compounds of Formula I are known to be useful in the treatment of diabetic complications. The process of this invention is set forth in Scheme 1. In general, the compounds of formula 1-4 of this invention are prepared as set forth therein.

Scheme 1

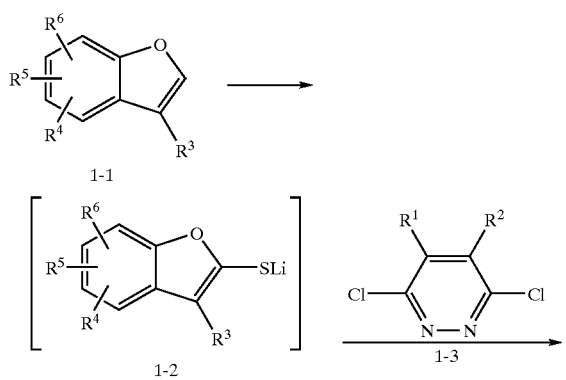

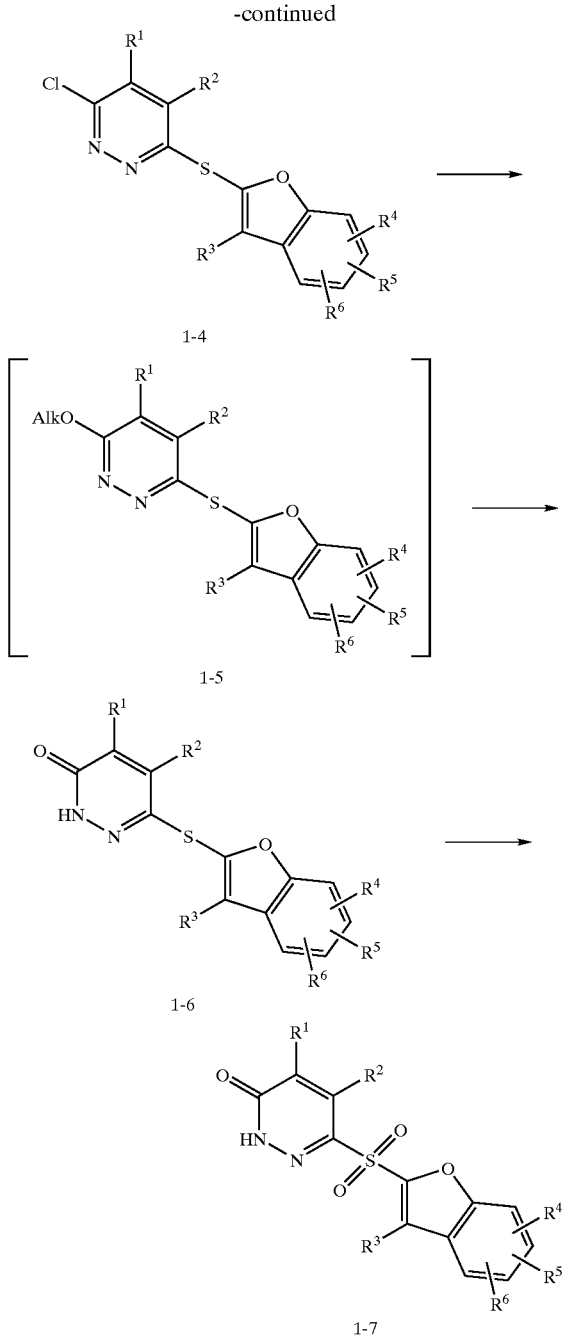

As set forth in Scheme 1, a compound of formula 1-4 is prepared as follows. An organolithium base such as n-butyllithium is added to a solution of a compound of formula 1-1 in a reaction inert solvent. Suitable reaction inert solvents include ether solvents such as dioxane, diethyl ether and tetrahydrofuran. Other suitable organolithium bases include methyl lithium, t-butyllithium, etc. The reaction mixture is stirred at a temperature of about −78° C. to about 0° C. for five minutes to about five hours. It is preferred to carry out the reaction in tetrahydrofuran at a temperature of about −40° C. for about one hour. The organolithium intermediate 1-2 is then formed by addition of a sulfur source such as sulfur powder (S$_8$). The reaction mixture is stirred at about −78° C. to about 0° C. for about one minute to about five hours and preferably at about −40° C. for about 5 minutes. The reaction mixture is warmed to about −20° C. to about room temperature and preferably to about 0° C. for about five minutes to about one hour and preferably for about 30 minutes. A solution of a compound of formula 1-3 in a reaction inert solvent as described above and preferably tetrahydrofuran is added and the resulting mixture is stirred at −20° C. to about room temperature and preferably at 0° C. The reaction mixture is warmed to room temperature over about one hour to about five hours and preferably for about two hours. The reaction mixture is then stirred at room temperature for a period of time, preferably one to five hours and most preferably for one hour. The desired compound is isolated from the reaction mixture as set forth in Example One below or according to other methods well known to those skilled in the art.

As shown in Scheme 1, a compound of formula 1-6 is prepared as follows. A compound of formula 1-4 is dissolved in a reaction inert solvent such as a (C$_1$–C$_2$) alkanol such as methanol or ethanol and is treated with a (C$_1$–C$_2$)alkoxide such as sodium methoxide or sodium ethoxide at about 40° C. to about the reflux temperature of the solution for about three hours to about twelve hours. It is preferred to use sodium methoxide in methanol at about 50° C. for about five hours. This forms the intermediate compound of formula 1-5, wherein Alk is (C$_1$–C$_2$)alkyl, which is subsequently treated with a mineral acid, preferably concentrated HCl, at about 40° C. to about reflux for about eight hours to about twenty hours. It is prefeable to reflux the reaction mixture for about fifteen hours. The desired compound of formula 1-6 is isolated from the reaction mixture as described in Example Two below or according to other methods well known to those skilled in the art.

As shown in Scheme 1, a compound of formula 1-7 is prepared as follows. A compound of formula 1-6 is dissolved in a reaction inert solvent, preferably an ether solvent such as tetrahydrofuran, diethyl ether or dioxane and is treated with an oxidizing agent. The oxidizing agent may be any reagent which is capable of oxidizing a sulfanyl group to a sulfonyl group, such as hydrogen peroxide, meta-chloroperbenzoic acid and other such reagents well known to those of ordinary skill in the art. It is preferable to use a urea hydrogen peroxide complex, in which case, the person of ordinary skill in the art will recognize that it will be desirable to use an activating agent such as trifluoroacetic anhydride in the reaction. The reaction is carried out in a reaction inert solvent such as tetrahydrofuran, dioxane or diethyl ether and preferably tetrahydrofuran. The reaction is carried out at a temperature of about 0° C. to about 35° C. with warming to about room temperature for about thirty minutes to about five hours. It is preferred to carry out the reaction at a temperature of 0° C. to about 25° C. with warming to room temperature for about two hours. The desired compound of formula 1-7 is isolated from the reaction mixture as described in Example Three below or according to other methods well known to those skilled in the art.

The starting materials and reagents for the above described compounds are also readily available or can be easily synthesized by those skilled in the art using conventional methods of organic synthesis. For example, many of the compounds used herein are related to, or are derived from, compounds found in nature, in which there is a large scientific interest and commercial need, and accordingly many such compounds are commercially available or are reported in the literature or are easily prepared from other commonly available substances by methods which are reported in the literature. In a specific example, 5-chloro-3- methylbenzofuran can be prepared according to methods well known to those of ordinary skill in the art or may be purchased from Amrutanjan (42-45, Luz Church Road, Mylapore, Chennai 600 004) or EMS Dottikon (CH-5606 Dottikon, Switzerland). 3,6-dichloropyridazine can be prepared by known procedures or purchased from Aldrich (P.O. Box 355, Milwaukee, Wis., 53201).

All journal articles, scientific references, patents and patent application publications cited herein are wholly incorporated by reference herein.

General Experimental Procedures

Melting points were determined on a Thomas-Hoover capillary melting point apparatus, and are uncorrected. Low-resolution mass spectra were obtained under thermospray (TS) conditions on a Fisons (now Micromass) Trio 1000 Mass Spectrometer (Micromass Inc., Beverly, Mass.), under chemical-ionization (CI) conditions on a Hewlett Packard 5989A Particle Beam Mass Spectrometer (Hewlett Packard Co., Palo Alto, Calif.), or under atmospheric pressure chemical ionization (APCI) on a Fisons (now Micromass) Platform II Spectrometer.

EXAMPLE ONE

3–Chloro-6-(5-chloro-3-methyl-benzofuran-2-ylsulfanyl)-pyridazine

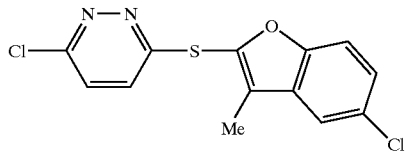

n-BuLi (47.7 mL, 119 mmol, 1.1 equiv) was added via an addition funnel to a solution of 5-chloro-3-methylbenzofuran (18 g, 108 mmol, 1 equiv) in tetrahydrofuran (125 mL) at −40° C. The reaction mixture was stirred at −40° C. for one hour and then sulfur powder (3.46 g, 108 mmol, 1 equiv) was added. After stirring at −40° C. for 5 min, the reaction mixture was warmed to 0° C. for 30 minutes. A solution of 3,6-dichloropyridazine (48.3 g, 324 mmol, 3 equiv) in tetrahydrofuran (50 mL) was added and the resulting mixture was stirred at 0° C. with warming to room temperature over two hours. The reaction mixture was then stirred at room temperature for an additional hour. The reaction mixture was concentrated to a low volume and ethanol (100 mL, about three volumes) and water (100 mL, about three volumes) was added to the residue. The mixture was granulated by stirring overnight. The solids were collected by filtration and repulped in ethanol (270 mL, about eight volumes) to afford the title compound of Example One as an off-white powder (29.1 g, 87%).

EXAMPLE TWO 6-(5–Chloro-3-methyl-benzofuran-2-ylsulfanyl)-2H-pyridazin-3-one

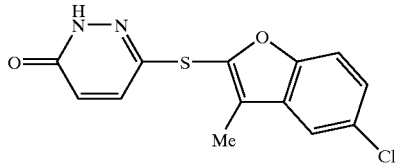

Sodium methoxide (299 mL, 1.31 mol, 5 equiv) was added to a slurry of 3-chloro-6-(5-chloro-3-methyl-benzofuran-2-ylsulfanyl)-pyridazine (the title compound of Example One) in methanol (500 mL, 6.1 vol). The resultant mixture was heated at 50° C. for five hours to provide, 3-(5-chloro-3-methyl-benzofuran-2-ylsulfanyl)-6-methoxy-pyridazine, which was not isolated. The reaction mixture was cooled to room temperature and concentrated hydrochloric acid (12N, 329 mL, 3.95 mol, 15 equiv) was added. The reaction mixture was heated at reflux for 15 hours and then cooled to room temperature. Water (400 mL) was added to the slurry and the mixture was cooled to 0° C. for 30 minutes. The solids were collected by filtration, dried under vacuum, and repulped in dichloromethane (600 mL, 8 vol) and isopropyl ether (150 mL, 2 vol) to afford the title compound of Example Two (71 g, 92%) as an off-white solid.

EXAMPLE THREE 6-(5-Chloro-3-methyl-benzofuran-2-sulfonyl)-2H-Pyridazin-3-one

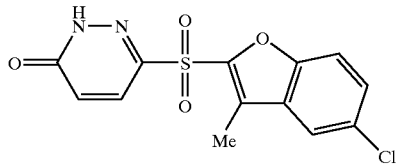

Trifluoroacetic anhydride (TFAA, 31.4 mL, 222 mmol, 6.5 equiv) was added to a slurry of 6-(5-chloro-3-methyl-benzofuran-2-ylsulfanyl)-pyridazin-3-ol (the title compound of Example Two, 10 g, 34.1 mmol, 1 equiv) and urea hydrogen peroxide complex (UHP, 19.3 g, 205 mmol, 6 equiv) in tetrahydrofuran (150 mL, 15 vol) at 0° C. TFAA was added at a rate which kept the temperature below 25° C. After addition was complete, the reaction mixture was warmed to room temperature for 2 hours. Water (200 mL, 20 vol) was added and the slurry was cooled to 0° C. The solids were collected by filtration and dried under vacuum to provide the title compound of Example Three (8.78 g, 79%) in two crops as a pale yellow solid.

What is claimed is:

1. A compound of the formula

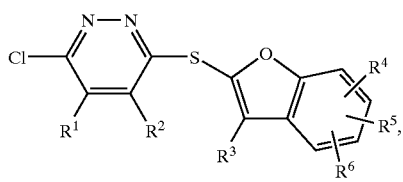

or a pharmaceutically acceptable salt thereof,
wherein $R^1$ and $R^2$ are each independently hydrogen or methyl; and
$R^3$, $R^4$, $R^5$ and $R^6$ are each independently H, halo, formyl, $(C_1-C_6)$alkyl optionally substituted with up to three fluoro, $(C_1-C_6)$alkoxy optionally substituted with up to three fluoro, $(C_1-C_6)$alkoxycarbonyl, $(C_1-C_6)$alkylenyloxycarbonyl, $(C_1-C_4)$alkoxy-$(C_1-C_4)$alkyl, $(C_1-C_4)$alkylcarbonylamido, $(C_3-C_7)$cycloalkylcarbonylamido, phenylcarbonylamido, benzyl, phenyl or naphthyl, wherein said benzyl, phenyl and naphthyl are optionally independently with up to two substituents independently selected from halo, $(C_1-C_6)$alkyl optionally substituted with up to three fluoro, $(C_1-C_6)$alkoxy optionally substituted with up to three fluoro and $(C_1-C_4)$ alkoxy-$(C_1-C_4)$alkyl.

2. A compound of claim 1, or a pharmaceutically acceptable salt thereof, wherein $R^3$, $R^4$, $R^5$ and $R^6$ are each independently hydrogen, methyl, methoxy, chloro, fluoro, ethyl, 4-fluorophenyl, trifluoromethyl, isopropyl or phenyl.

3. A compound of claim 2, or a pharmaceutically acceptable salt thereof, wherein $R^1$, $R^2$, $R^4$ and $R^5$ are each hydrogen; $R^3$ is 3-methyl and $R^6$ is 5-chloro, having the structure

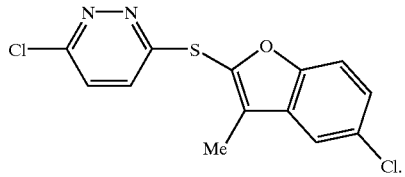

4. A process for preparing a compound of the formula

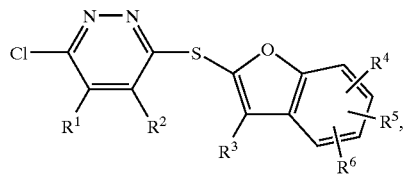

IV wherein $R^1$ and $R^2$ are each independently hydrogen or methyl;

$R^3$, $R^4$, $R^5$ and $R^6$ are each independently H, halo, formyl, ($C_1$–$C_6$)alkyl optionally substituted with up to three fluoro, ($C_1$–$C_6$)alkoxy optionally substituted with up to three fluoro, ($C_1$–$C_6$)alkoxycarbonyl, ($C_1$–$C_6$)alkylenyloxycarbonyl, ($C_1$–$C_4$)alkoxy-($C_1$–$C_4$)alkyl, ($C_1$–$C_4$)alkylcarbonylamido, ($C_3$–$C_7$)cycloalkylcarbonylamido, phenylcarbonylamido, benzyl, phenyl or naphthyl, wherein said benzyl, phenyl and naphthyl are optionally independently with up to two substituents independently selected from halo, ($C_1$–$C_6$)alkyl optionally substituted with up to three fluoro, ($C_1$–$C_6$)alkoxy optionally substituted with up to three fluoro and ($C_1$–$C_4$)alkoxy-($C_1$–$C_4$)alkyl;

comprising the consecutive steps of:

(a) reacting a compound of the formula

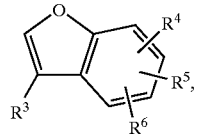

II wherein $R^3$, $R^4$, $R^5$ and $R^6$ are each independently defined as set forth above, with an organolithium compound in the presence of a sulfur source in a reaction inert solvent to form a reactive intermediate of the formula

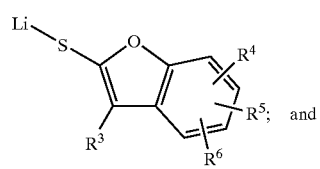

IIa (b) reacting said reactive intermediate IIa with a compound of the formula

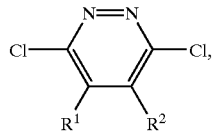

III to form a compound of the formula IV.

5. A process of claim 4 wherein said organolithium compound is n-butyllithium, said reaction inert solvent is tetrahydrofuran and said sulfur source is $S_8$.

6. A process of claim 4 or 5 wherein $R^3$, $R^4$, $R^5$ and $R^8$ are each independently hydrogen, methyl, methoxy, chloro, fluoro, ethyl, 4-fluorophenyl, trifluoromethyl, isopropyl or phenyl.

7. A process of claim 6 wherein $R^1$, $R^2$, $R^4$ and $R^5$ are each hydrogen; $R^3$ is 3-methyl and $R^6$ is 5-chloro.

8. A process for preparing the compound of the formula

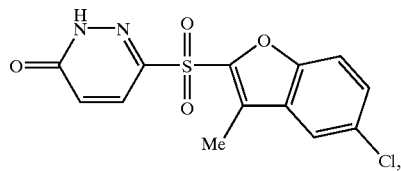

XI comprising the consecutive steps of:

(a) reacting the compound of the formula

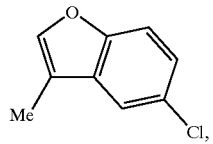

with n-butyllithium in the presence of $S_8$ in tetrahydrofuran to form the reactive intermediate

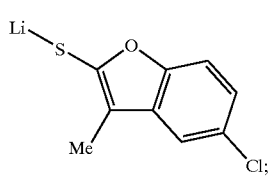

XIIa (b) reacting said reactive intermediate XIIa with the compound of the formula

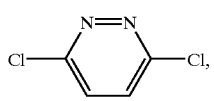

XIII to form the compound of the formula

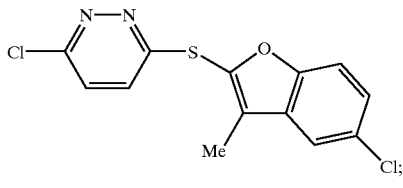

XIV (c) reacting said compound of the formula XIV with sodium methoxide in methanol to form the compound of the formula

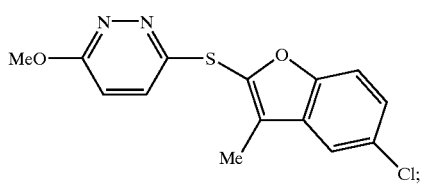

XV (d) reacting said compound of the formula XV with concentrated hydrochloric acid to form the compound of the formula

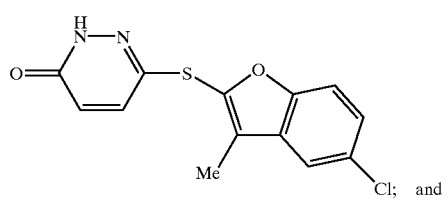

XVI and (e) oxidizing said compound of the formula XVI with hydrogen peroxide urea complex in the presence of trifluoroacetic anhydride in tetrahydrofuran to form a compound of the formula XI.

9. The process of claim 8 wherein step (c) and step (d) are performed in situ.

10. A process for preparing a compound of the formula

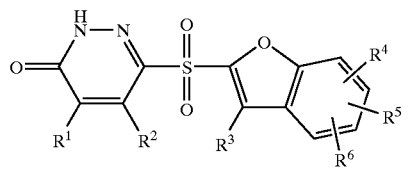

I wherein $R^1$ and $R^2$ are each independently hydrogen or methyl; and $R^3$, $R^4$, $R^5$ and $R^6$ are each independently h, halo, formyl, $(C_1-C_6)$alkyl optionally substituted with up to three fluoro, $(C_1-C_6)$alkoxy optionally substituted with up to three fluoro, $(C_1-C_6)$alkoxycarbonyl, $(C_1-C_6)$alkylenyloxycarbonyl, $(C_1-C_4)$alkoxy-$(C_1-C_4)$alkyl, $(C_1-C_4)$alkylcarbonylamido, $(C_3-C_7)$cycloalkylcarbonylamido, phenylcarbonylamido, benzyl, phenyl or naphthyl, wherein said benzyl, phenyl and naphthyl are optionally independently with up to two substituents independently selected from halo, $(C_1-C_6)$alkyl optionally substituted with up to three fluoro, $(C_1-C_6)$alkoxy optionally substituted with up to three fluoro and $(C_1-C_4)$alkoxy-$(C_1-C_4)$alkyl;

comprising the consecutive steps of:

(a) reacting a compound of the formula

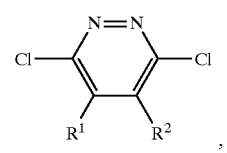

II wherein $R^3$, $R^4$, $R^5$ and $R^6$ are each independently defined as set forth above, with an organolithium compound in the presence of a sulfur source in a first reaction inert solvent to form the reactive intermediate

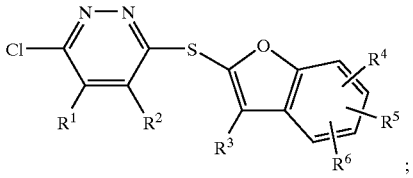

IIa (b) reacting said reactive intermediate IIa with a compound of the formula

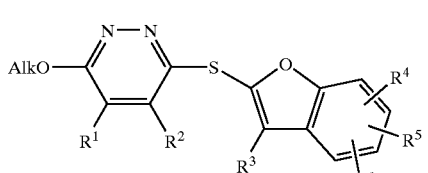

III to form a compound of the formula

IV (c) reacting said compound of the formula IV with an alkaline $(C_1-C_2)$alkoxide in a $(C_1-C_2)$alkanol to form an ether compound of the formula

V wherein Alk is $(C_1-C_2)$alkyl;

(d) reacting said compound of the formula V with a mineral acid to form a compound of the formula

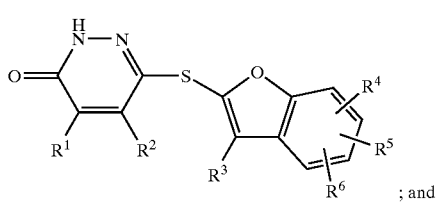

VI

; and (e) oxidizing said compound of the formula VI in a second reaction inert solvent to form a compound of the formula I.

11. The process of claim 10 wherein step (c) and step (d) are performed in situ.

12. The process of claim 11 wherein in step (a) said organolithium compound is n-butyllithium, said first reaction inert solvent is tetrahydrofuran and said sulfur source is $S_8$; in step (c) said alkaline $(C_1-C_2)$alkoxide is sodium methoxide and said $(C_1-C_2)$alkanol is methanol; and in step (d) said compound of formula VI is oxidized with urea-hydrogen peroxide in the presence of trifluoroacetic anhydride and said second reaction inert solvent is tetrahydrofuran.

13. A process of any one of claims 10–12 wherein $R^3$, $R^4$, $R^5$ and $R^6$ are each independently hydrogen, methyl, methoxy, chloro, fluoro, ethyl, 4-fluorophenyl, trifluoromethyl, isopropyl or phenyl.

14. A process of claim 13 wherein $R^1$, $R^2$, $R^4$ and $R^5$ are each hydrogen; $R^3$ is 3-methyl and $R^6$ is 5-chloro.

* * * * *